(12) United States Patent
Kocher

(10) Patent No.: US 6,652,455 B1
(45) Date of Patent: Nov. 25, 2003

(54) METHOD AND APPARATUS FOR SCANNING OF FOOD AND MEDICINE TO PROVIDE OUTPUTS RELATIVE TO A USER PROFILE

(76) Inventor: Jean-Pierre Kocher, 2645 California St., #212, Mountain View, CA (US) 94040

( * ) Notice: Subject to any disclaimer, the term of this patent is extended or adjusted under 35 U.S.C. 154(b) by 0 days.

(21) Appl. No.: 09/635,856

(22) Filed: Aug. 11, 2000

Related U.S. Application Data

(60) Provisional application No. 60/148,676, filed on Aug. 13, 1999.

(51) Int. Cl.[7] .............................. A61B 5/00; G06F 17/00
(52) U.S. Cl. ........................ 600/300; 235/375; 128/921; 708/132
(58) Field of Search .............................. 600/300, 301, 600/481, 500, 529, 587; 705/2–3, 9; 128/903, 904, 920–925; 235/462.25, 375; 708/130–134; 340/539.1–539.13, 539.16–539.19, 573.1

(56) References Cited

U.S. PATENT DOCUMENTS

| | | | |
|---|---|---|---|
| 4,857,713 A | 8/1989 | Brown | |
| 5,845,255 A | 12/1998 | Mayaud | |
| 5,954,640 A | * 9/1999 | Szabo | 128/921 |
| 6,024,281 A | * 2/2000 | Shepley | 235/375 |
| 6,050,940 A | * 4/2000 | Braun et al. | 600/300 |
| 6,375,077 B1 | * 4/2002 | Hankins et al. | 235/462.45 |

FOREIGN PATENT DOCUMENTS

| | | |
|---|---|---|
| GB | 2285135 | 6/1995 |
| GB | 2313940 | 12/1997 |
| WO | 99/10829 | 3/1999 |

\* cited by examiner

*Primary Examiner*—Max F. Hindenburg
*Assistant Examiner*—Michael Astorino
(74) *Attorney, Agent, or Firm*—Rader, Fishman & Grauer PLLC

(57) ABSTRACT

A method and apparatus for recording foods and medicines by scanning and relating scanned data to a stored medical profile specific to an individual. In a preferred embodiment, quantities of foods or medicines are sensed by scanning to relate consumption data or interaction data when a user should be aware of possible adverse interactions. Various types of databases are disclosed. Wireless transfer of data is contemplated, with location of consumption recorded and transferred as well in a particular embodiment.

34 Claims, 9 Drawing Sheets

| ITEMS DATABASE | MEDICAL PROFILE DATABASE | OUTPUT ANALYSIS |
|---|---|---|
| FOOD (Product Scan) | ALLERGIES (Input Manually) | WARNING AS A FUNCTION OR TYPE, QUANTITY AND INPUT PROFILE, Based on Scanned Product Information |
| MEDICINE (Product Scan) | MEDICINE (Input Manually or by Prior Items Database Scan) | MEDICINE/MEDICINE INTERACTIONS Based on Scanned Product Information |
| FOOD (Product Scan) | MEDICINE (Input Manually or by Prior Items Database Scan) | FOOD/MEDICINE INTERACTIONS Based on Scanned Product Information |

| ITEMS DATABASE | MEDICAL PROFILE DATABASE | OUTPUT ANALYSIS |
| --- | --- | --- |
| FOOD (Product Scan) | ALLERGIES (Input Manually) | WARNING AS A FUNCTION OR TYPE, QUANTITY AND INPUT PROFILE, Based on Scanned Product Information |
| MEDICINE (Product Scan) | MEDICINE (Input Manually or by Prior Items Database Scan) | MEDICINE/MEDICINE INTERACTIONS Based on Scanned Product Information |
| FOOD (Product Scan) | MEDICINE (Input Manually or by Prior Items Database Scan) | FOOD/MEDICINE INTERACTIONS Based on Scanned Product Information |

FIG. 4

METHOD AND APPARATUS FOR SCANNING OF FOOD AND MEDICINE TO PROVIDE OUTPUTS RELATIVE TO A USER PROFILE

"This application claims the benefit of the U.S. Provisional Application No. 60/148,676, filed Aug. 13, 1999."

BACKGROUND OF THE INVENTION

1. Field of Invention

This invention relates to a method and apparatus for recording foods or medicines by scanning for analysis. More particularly, this invention relates to a method and apparatus for recording information associated with for foods or medical commodities for indicating a caution to their consumer. Still more particularly, this invention relates to a method and apparatus for relating recorded information with consumption data by amount or interaction data indicating when a user should be aware of possible adverse interactions. Still more particularly, this invention relates to a method and apparatus for relating scanner-generated data with a database uniquely related to a particular individual for consumption information, particularly related to amounts and quantities of consumed goods. Data collection may be made by a barcode scanner, while data transmission may be hard-wired or wireless, such as by global positioning system (GPS) transmission.

2. Description of Related Art

In U.S. Pat. No. 5,819,735, assigned to the applicant of this application, a portable autonomous electronic device is described, along with a method of use. The device contains a barcode scanner, a nutrition facts database, a memory for recording products consumed, and a readout display. The device thus permits a consumer to scan barcodes on purchased food items to record consumption and to preserve and report a cumulative total of calories and other consumables.

There remains a need from a consumer's viewpoint for providing other types of medically related information, from the food contents of an item purchased, to a wide variety of personal situations. For example, food allergies often exist to an item, such as peanuts, which can trigger severe and sometimes fatal allergic or asthmatic reactions when the item is not readily recognized as being present. As a simple example, a cooking oil may have a peanut oil base unknown to the user. It would thus be convenient if foods generally could be related to such allergies initially at a point of purchase as well as at the time of consumption.

There also remains a need from a consumer's viewpoint to scan food items that do not necessarily have barcodes. Many food labels do not have barcodes, instead having other types of data such as text or handwriting.

Databases are known which contain medically related information that permits a consumer ready access. One such database permitting a search of a large number of different health areas is known as "Healthlink USA". In general, such databases are encyclopedic in nature primarily conveying information. However, there exists at least one disease specific database for persons having celiac disease or gluten intolerance that contains a list of gluten-free foods. Users of the database thus make purchase/no purchase decisions on the basis of the presence or absence of gluten in a food of interest.

A second shortcoming in the prior approach to using product information relates to medicine-to-medicine interactions, which can be fatal. Such programs are available to a pharmacist or supermarket for indicating by specific drug information, whether generic or brand name, what precautions and interactions might exist. For example, a person taking a Coumadin brand blood thinner should be warned against additionally taking quantities of aspirin, which can exist in other forms such as cold medicines. Thus, it would be convenient if such medicine-to-medicine interactions could be indicated by scanning and using barcode information now readily available for inventory control by pharmacists and supermarkets. Moreover, it would be convenient if such interaction databases were tailored for an individual's specialized needs.

Still a third shortcoming in the prior art, now emerging as an area of public health interest, relates to a food/medicine interface. Recently, seemingly innocuous food items, such as grapefruits and grapefruit juice, have worried some reporting services as either increasing or decreasing human uptake of certain medicines. Whether the effect is enhanced, leading to risky over-medication situations, or inhibited, leading to equally risky under-medication possibilities has, as far as reasonably known, not been related by the use of product information for the convenience of individuals.

In addition, the use of such collected information for conveniently scheduling ingestion by a patient or individual of information stored should enhance taking medicines on time and in a correct quantity.

Finally, a use of the invention currently perceived as useful is in a collection of information for use by healthcare individuals of information from repetitive scans by consumers. Thus, an improvement in a medical situation might more readily be related to food or medicine contents by use of barcode scanning.

BRIEF SUMMARY OF THE INVENTION

A basis for this invention is the notion of relating scanned data information for products and commodities to a database of information related to the product, such information being of interest to a consumer. The type of information in the database may be encyclopedic, collected, or accumulated information intended to provide sub-information to the consumer according to the consumer's interest. The information can be scanned from barcodes, or text, or handwriting using an optical scanner. In its broadest aspect, the invention is directed to a recording device for food items or medication intake, where the items are identified by means of a scanner, such as but not limited to, a barcode scanner. The device records the scanned data, the serving size (set by the user), and the time and date of consumption in memory. Optionally, a UPC barcode is used to extract from database information related to the item such as the product name, the brand name, and the recommended or default serving size, nutrients and chemical components included in the product, and manufacturing processes that could affect the health of the user. Consumption schedules are optionally set for each individual item and are stored in memory. This latter option is used to indicate or to warn the user when consumption of items is required or to monitor over/under consumption of some items from a dietary point of view.

In another aspect of the invention, the recording device identifies food items by scanned data, such as, but not limited to, data from a barcode scanner. The database contains information about the recorded food items, while the memory preferably contains profile data about the consumer. Such profiled information may typically include allergic reactions to shellfish, peanuts, whole milk, yeast-based items, and other foodstuffs for which allergic contraindications are made relative to a particular consumer. At another level, the database includes information about food contents and quantity sufficient to institute a warning, such as the number of milligrams of iodine in a particular shellfish portion and the number of portions.

In still another aspect of the invention, the recording device identifies medicines, such as prescriptions, by its scanned data. The database contains information about the medicine, and about other medicines ingested by the consumer, either input directly or as a result of prior scans. Such profiled information is then used to indicate, by such scanned information, typical or specific medicine-to-medicine interactions. By the term "specific", it is intended to include reactions from a medicine or specific drug information pertinent to the individual and stored into the memory for comparison with the scanned data.

In still another feature of the invention, the device proceeds as aforementioned to scan foods and medicines. The memory includes a database of information interrelating adverse or possibly adverse interface reactions between foods and medicines as seen according to the barcodes.

In yet another feature of the invention, collected information is transferred from the handheld or palmtop computer to a larger centralized computer storage facility to collect information suitable for public health services. Such information would be available with the permission and consent of the individual. This information can be transferred via a physical connection, or can be transferred between a hand-held or palm-top computer and a larger computer through a wireless interface, including but not limited to a GPS link to determine location of the information transferred, or its source.

According to any of the aforementioned aspects of the invention, there are significant advantages. The device scans the product information to identify items so that no typing or manual input is needed. The consumer or user is able to extract from a database in RAM any pertinent item information, such as name, brand, content, nutritional information, and the like and to display such information to check the accuracy and desirability of the product scanned. By way of a simple example, a user at a supermarket selecting peanut oil may wish to scan the label of the item to see if the device produces an adverse warning against the purchase according to the stored information.

The method and apparatus of the invention allow one to set the serving size consumed to track more precisely the items consumed and the amount, so that adverse reactions and interactions according to amount can be obtained. By way of an example, a person limited to two (2) mg of salt per day for blood pressure reasons, using the device on a real time basis according to amount of scanned food consumed, is better informed about the content of foods and when such foods consumed may reach the preferred salt limit.

By use of the device and method according to the invention, a user is able to record, over a long period of time, consumed items, the consumed serving size, time, date, and location of consumption. In a typical use of the invention, it is able to warn the user when consumption time, such as for medicines, is due, or warn the user when over/under consumption occurs. In addition, the user may store a user medical profile to detect potential allergy or incompatibility with consumed items, and to warn again of food and drug interference. Moreover, the user may later download by means of an interface the recorded information for further analysis; in this respect, a significant advantage for the invention is its use for compiling data over selected periods of time, either for personal information or the information of others such as medical practitioners or public health officials. Moreover, the use of removable memory (PCMCIA SRAM or Flash Memory Cards) to store databases makes it convenient to either change or update the databases.

Finally, the clock can be adjusted. In still another aspect of the invention, data transmission between a scanner, a database, and a central data collection facility may be wireless, and may store any other pertinent information available using a GPS system. In a typical example, the location of consumption can be collected by such scanned information to amass geographical data of interest to later analysis.

These and other objects, features, advantages, and uses of the method and apparatus according to the invention will also become apparent from a detailed review of the drawings and the description of the preferred embodiments that follow.

BRIEF DESCRIPTION OF THE DRAWINGS

FIG. 4 is a 3×3 matrix of a summary of features of the invention.

DESCRIPTION OF THE PREFERRED EMBODIMENTS

Figure 1A:
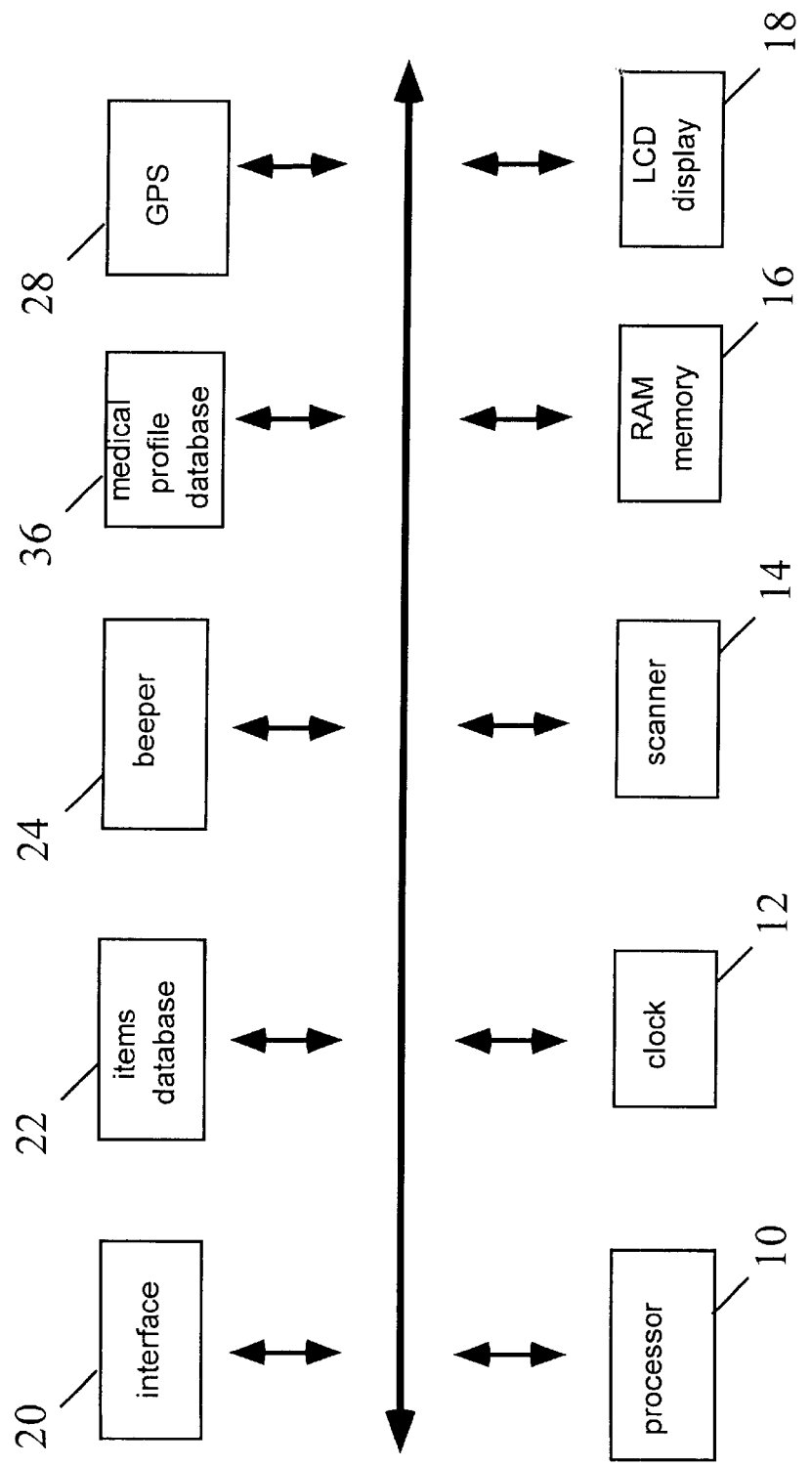
FIG. 1a is a simplified block diagram of the electronic components for an apparatus according to the invention for practicing the described method according to the invention.
Figure 2:
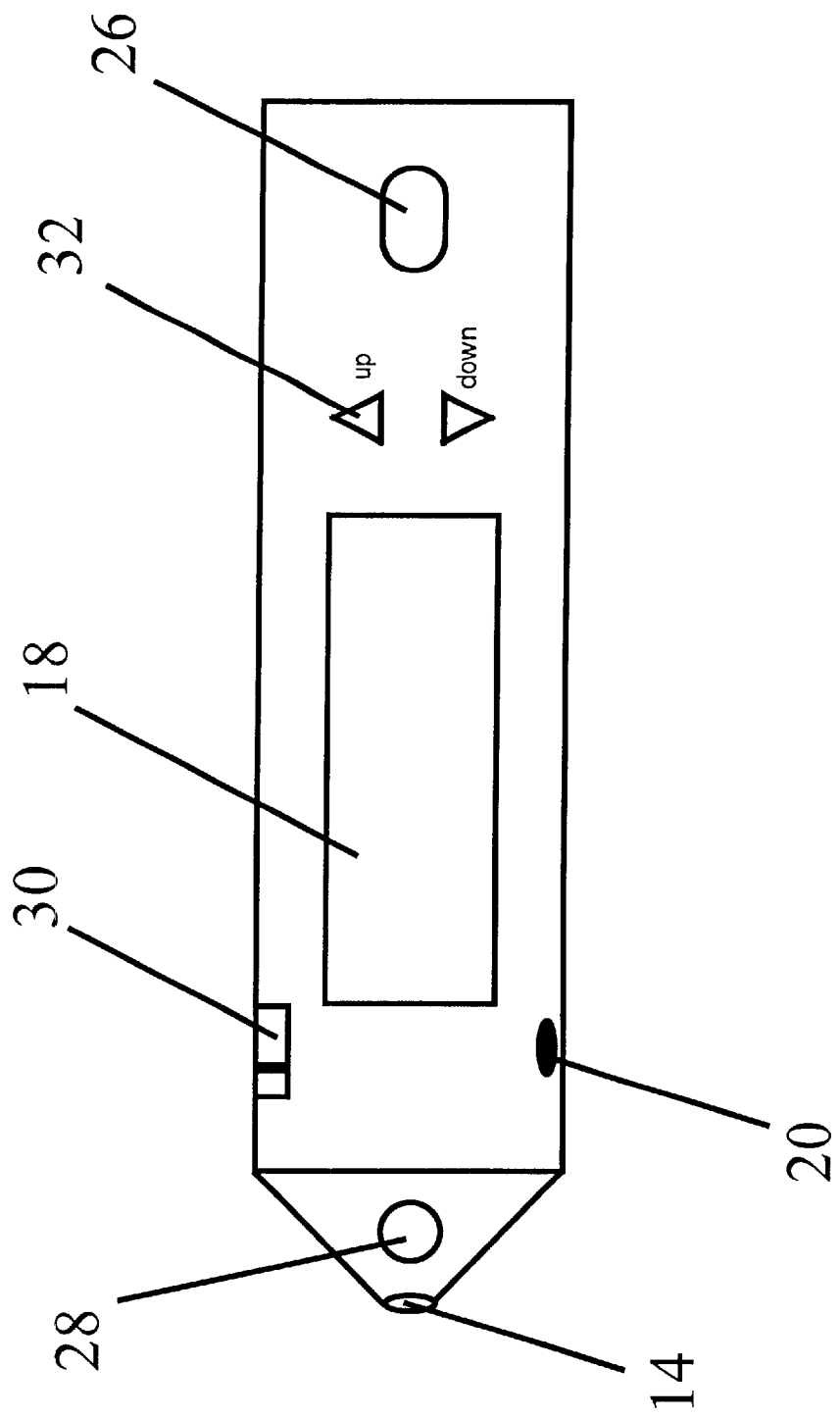
FIG. 2 shows an example of a plan view of the preferred device assembly.

Referring to FIGS. 1a and 2, the apparatus according to the invention includes a processor 10, a clock 12, a scanner 14, a memory 16, an LCD display 18, an interface 20, an items database 22, a beeper 24, a validation switch 26, a scanner switch 28, a multi-way switch 30, up and down set switches 32, and a medical profile database 36, interconnected in an operative manner. The apparatus is thus structurally similar to the apparatus shown in the applicant's prior patent, U.S. Pat. No. 5,819,735 incorporated herein by reference as is fully repeated here, but including an items database 22 and a medical profile database 36.

The clock 12 is preferably a 24-hour clock, but a shorter time can be selected if desired. The items database 22 is preferably a RAM storing the input received from the scanner 14, but other types of storage media may also be used. In the prior patent, a general nutrition fact database was disclosed; here a medical profile database is disclosed instead to effect the features of this new invention.

The description that follows relates to a general identification of the invention as thus shown in FIG. 1. Specific identification of microchips, scanners and other elements used in the manufacture of the device, or the manner of interconnecting the elements, are not shown in detail in the drawings or described in the specification.

Such components and their operative assembly are well known to one of ordinary skill in the art when considering this written description of the invention. Another reason for this is that technological advances are very rapid and materials that can be obtained and used at the outset of development may be expected to be readily superseded by newer and more advanced technology. A third reason is that at any given time, a person skilled in electronics or computer design can select the most appropriate components and methods for connecting them, to construct the device described after careful study of the description that follows.

Figure 1B:
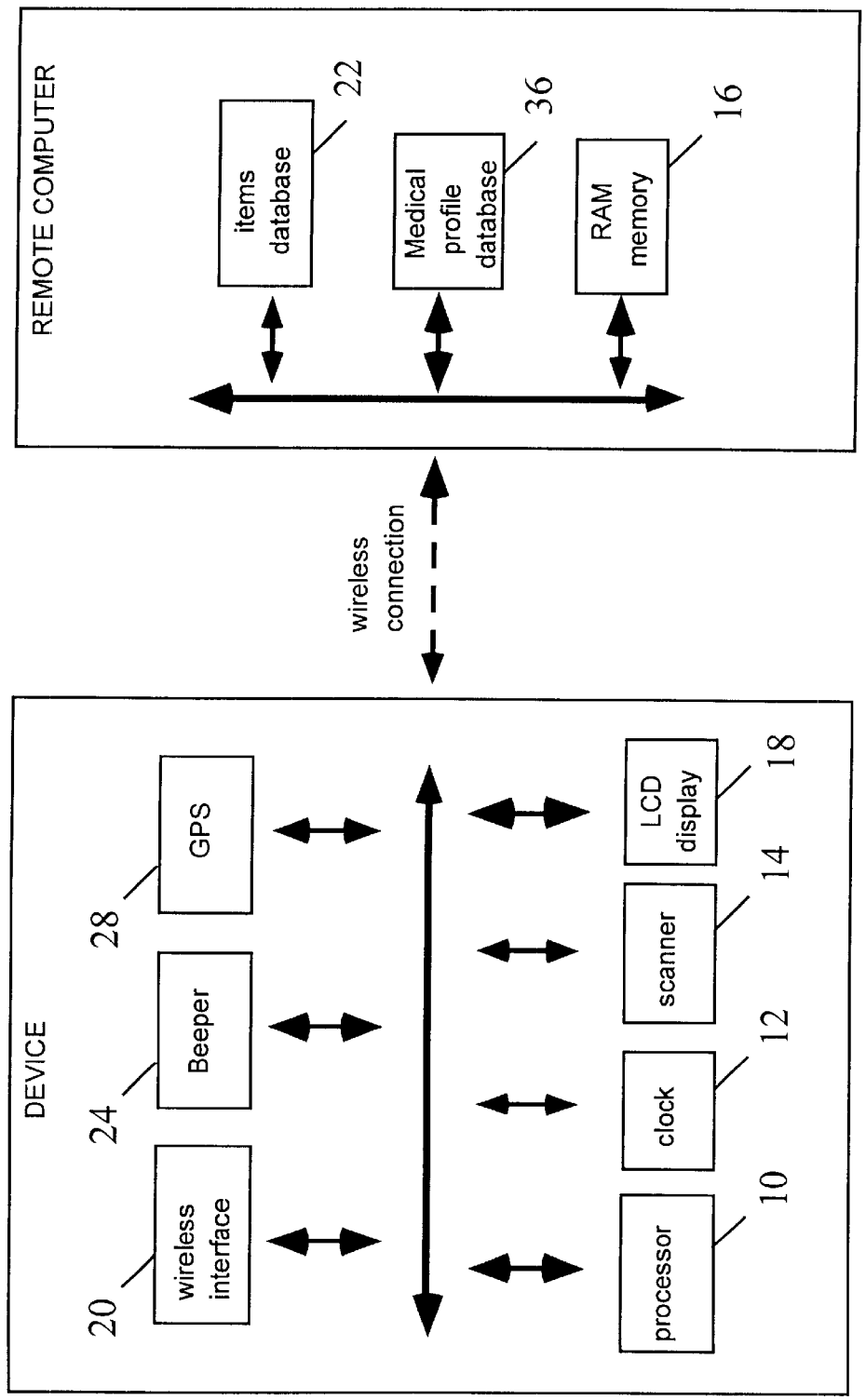
FIG. 1b is a simplified block diagram showing data exchange between a device according to the invention and a remote computer.

FIG. 1b illustrates that the apparatus of FIG. 1a may comprise a device itself, and a remote computer having the items database 22, the medical profile database, and the memory 16 at a location separate from the device. While the device and a remote computer can be hardwired in a conventional matter, such as transferring data by telephone lines, the invention also contemplates using a wireless connection as seen in FIG. 1b. Moreover, the wireless connection may include a GPS system for ascertaining the location of scanned data sensed by the device and transferred to a remote computer.

In the preferred embodiment and according to FIGS. 1 and 2, the system consists of means such as a processor 10 under the control of a pre-stored program, incorporating means for entering product identification, such as an optical scanner 14. A scanner on-switch 28 activates the scanner 14. The scanned data is then related to its respective product information that is stored in databases on one or more removable memory modules 22. Those modules 22 may either be on the device or at the central computer.

This items database 22 can include barcode numbers and other related information such as the name, product, suggested serving size, nutrients and chemicals included in the product, and processing techniques that may have an incidence on an individual's health. This information can be entirely or partly displayed on a screen 18. By way of example, the stored information may relate to: (1) a database of allergies; (2) medicinal items; and (3) restaurant foods. Collecting data relating to these three matters may help determine which allergies are triggered by which restaurant foods, and by using GPS techniques, at a given location.

The device will also relate data included in the items database 22 such as nutrients and chemicals content of the product with the medical profile stored in the medical profile database in the memory 36 in order to warn the user from possible allergy or incompatibility to some items consumed. Alternatively, the database 22 may be a specific medicine profile, such as one individually entered specific for the user, or one derived from medicine barcodes, including prescription barcodes, derived from prior barcode scans of prior purchases. Moreover, the database in the medical profile database may include interactions between foods and medicines, to provide an output upon a scan of the food or medicine item by the scanner 14. Moreover, the medical profile database 36 may include a database of nutrients, such as lookup tables of protein, fat, and carbohydrates for individual serving items found by the scanner to produce information of value when consumed at the consumer level.

Such information may be diet-related, such as calories, or health-related, such as sodium, fats, or the like.

The processor 10 is connected in a known manner to a suitable storage means such as a user memory 16 where product records of all products consumed over a period of time are kept. These product records can include barcode number, the amount of consumed servings, time, date, and location of consumption, for example. The time and date are provided by means such as a 24-hour clock 12. The location of the product consumption can be provided via relations with the GPS system, as discussed in connection with FIG. 1b. The user may also store in the user memory 16 a consumption schedule for one or several items and a consumption goal per period of time. The device can warn the user if this goal has not been reached or has been passed, or if the consumption time is due, by the mean of an audible beeper 24 or other suitable alarm or warning device or technique.

An interface 20, such as a serial or parallel port or infrared or other wireless transmitter, is used to exchange data between this device and an external device, for the purpose of updating both databases or for transferring recorded data, personal data, and settings to a remote location. Such a capability is advantageous in that large amounts of data about an individual's consumption needs are related to food or medicine or goods consumption.

As shown in FIG. 2, the main embodiment of the device also incorporates means such as a 6-way switch 30 for changing the mode that the user wishes to set, with choices including input of data derived from scanned items, correcting input, setting time, scheduling item consumption, and interfacing with an external device. In order to change parameters such as serving size consumed by the user, means such as a set switch 32 is provided. A validation switch 26 is provided for validating any operation or setting. Display means such as an LCD display 18 shows items and related information.

This invention specifies an electronic device that is preferably portable, for example by a palm-top computer plus a scanner or fixed or portable personal computer or microprocessor. The most preferred embodiment incorporates a processor 10, an integral scanner 14, a clock 12, a display 18, preferably of the LCD type, a user memory 16, a removable memory 22 containing items information in a database and a removable memory 36 storing the user medical profile. FIG. 2 represents one construction of the invention, but other constructions and configurations are possible.

The method of operation described herein is given merely as an example of how the device could be constructed and used. It is not meant to limit the scope of either the hardware or the software components of the invention, nor to limit the method of operation to the steps described here.

Modes can be selected on the device using 6-way switch 30: (a) an input mode, in which the input mode is used to record new items consumed; (b) a time/date mode to set the time and date parameters; (c) a correction mode to correct data input by error or which later needs to be deleted; (d) a schedule set mode to enter schedules for items intake; (e) a medical profile update mode to update the user's medical profile; and (f) a transfer mode to transfer data stored in device's memory to a remote location.

Figure 3A:
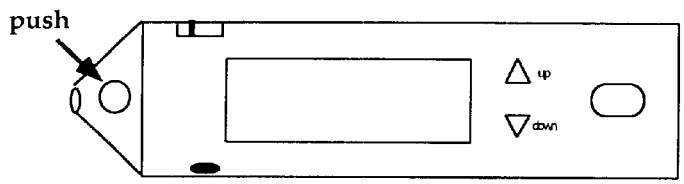
FIGS. 3A and 3B show an example of the operation for inputting product information for consumption.

Mode I: Input (FIG. 3A) To scan a new item, the 6-way switch 30 is placed in the "input" position. The integral optical or laser scanner 14, preferably of the wand type, but otherwise of the laser or CCD or other type, is used to scan the item's relevant product information into the device. The scanner is activated by depressing and holding down the scanner on-switch 28 and passing the scanner 14 over the item's label. Using the scanned information, the processor 10 performs an automatic search in the database 22, to retrieve the information pertaining specifically to the product scanned. Information such as the name of the product, the default serving size (as suggested by the product provider) will be shown on the display 18.

In the meantime, the allergy, or incompatibility between the user and the scanned item will be checked by comparing data stored in the medical profile and desired nutrient and chemical content of the item. Data stored in the medical profile database 36 can also be used to fine-tune the suggested serving size extracted from the item database (for instance, when this serving size is depending upon the age or the weight of the user).

The serving size consumed can be adjusted using the set switches 32. When the correct serving size value is displayed and the servings choice is entered, the validation switch 26 is depressed to enter and record into memory the scanned data, the number of servings, the time, the date, and if desired the location for a GPS-compatible system.

Figure 3B:
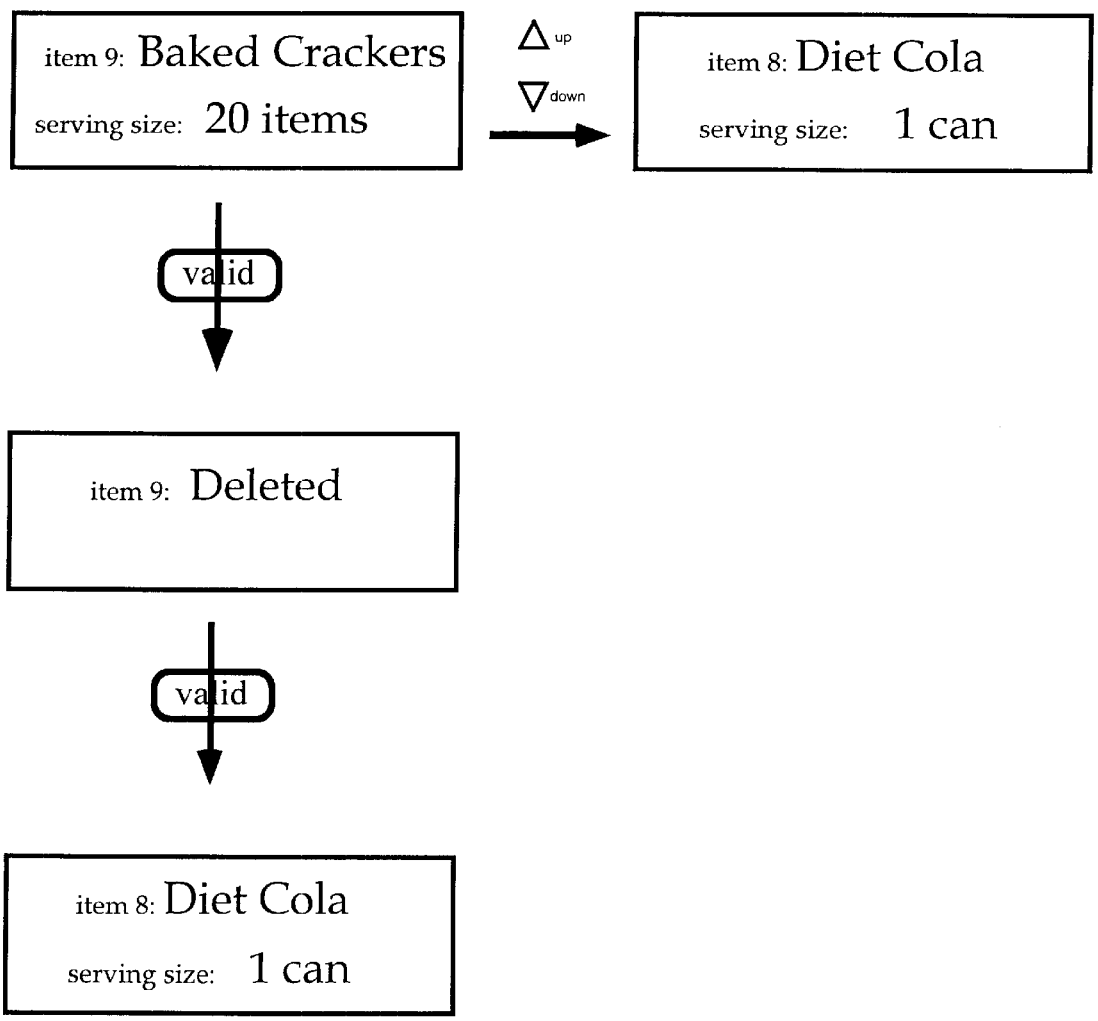

Mode II: Correction (FIG. 3B) The product number, serving size and time/date of entry records for each product entered are saved in the memory 16 of the device.

However, once an item is entered and validated, it may subsequently be deleted by using the "correct" function. In a correction mode, the product record of any previously entered product of the day can be deleted. To delete an item, the 6-way switch 30 is moved to the "correct" position. The name and serving size of the last item entered will be displayed on the display 18. To select an item to delete that was entered previously to the last item, set switch 32 is turned until the item desired to be deleted appears on the display 18. To delete the item displayed, the validation switch 26 is depressed. The record related to the deleted items is removed from the memory 16 and the words "deleted" are displayed.

Figure 3C:
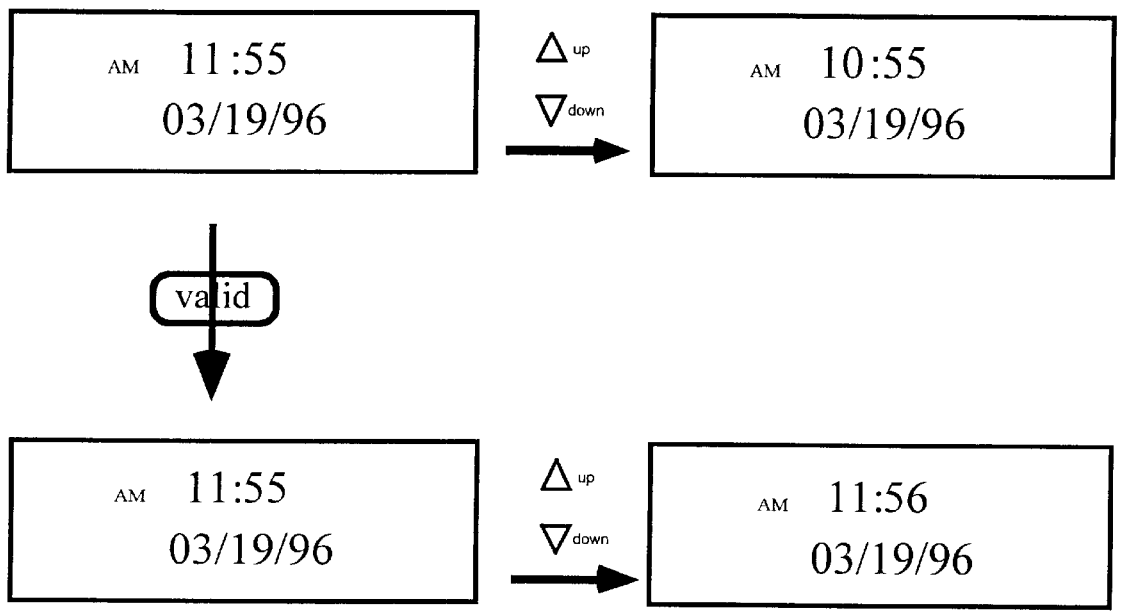
FIG. 3C shows the operation of setting the time and date for the apparatus according to the invention.

Mode III: Time/date setting (FIG. 3C) The device includes a clock 12. Time and date are recorded with the specific data related to each items scanned into memory 16. Therefore, it is important to have the time/date functions set to the appropriate values. To set the time and date, the 6-way switch 30 must be set on "time set". When this mode is selected, the "hour" portion of the clock will begin to blink. The set switches 32 are actuated to change the numerical value of the blinking portion. When the correct number has been chosen, the validation switch 26 is depressed and the next value, "minutes", is displayed. Each value (hours, minutes, day, date and year) is set as described above, depressing validation switch 26 when the correct numerical value has been chosen.

Figure 3D:
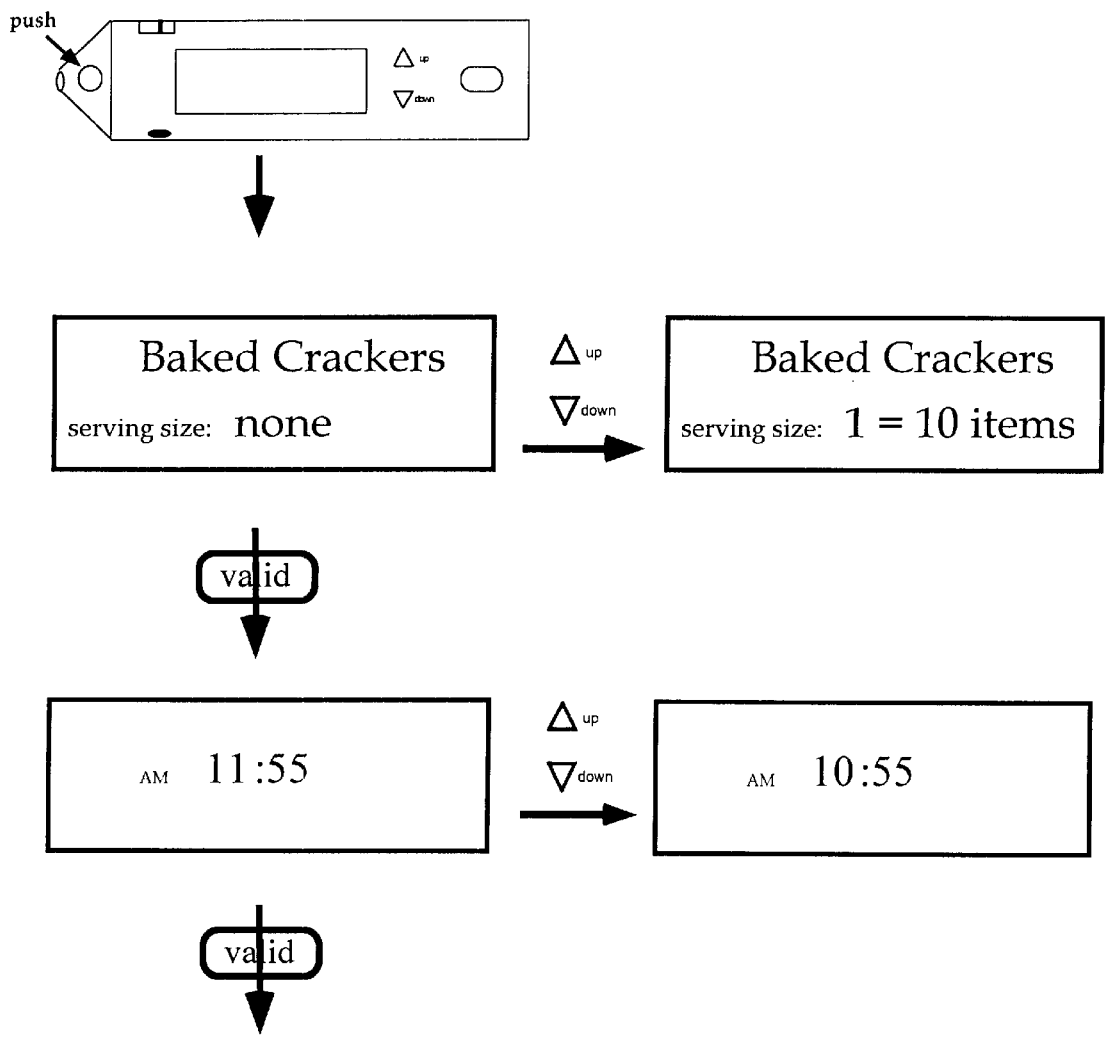
FIG. 3D shows a typical example of the operation for correcting input data and for setting a consumption schedule.
Figure 3D:
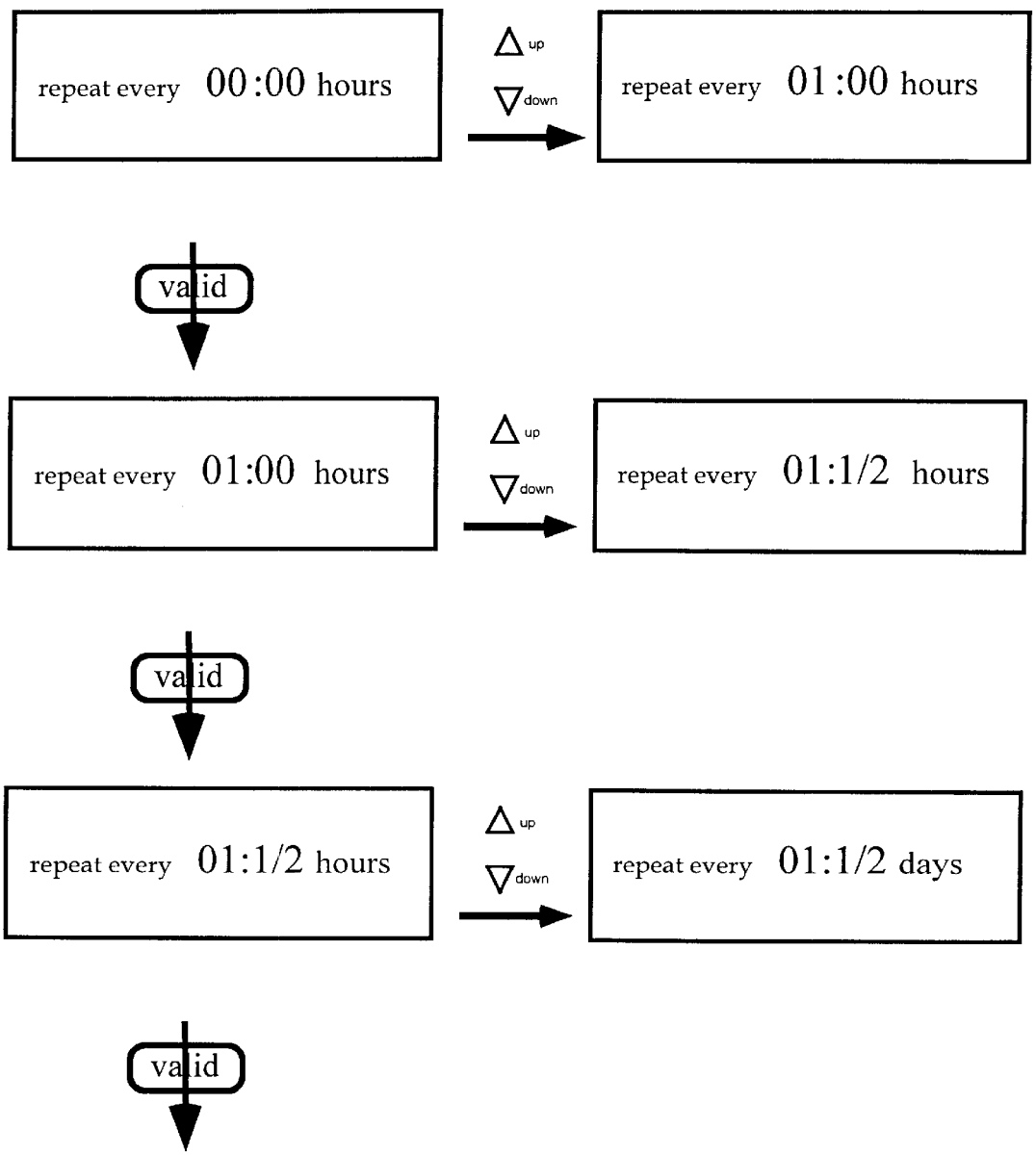

Mode IV: Scheduling (FIG. 3D): The consumption for one or several items can be scheduled and stored into the device memory. When an item consumption has been scheduled, the device can warn the user when the consumption time is due. If during the scheduling process, the user has selected a serving size, the device will be able to warn the user for under or over consumption of this item.

To attach a schedule to a given item, the 6-way switch 30 must be set on "scheduling". The item is then scanned by depressing and holding down the scanner on-switch 28 and passing the scanner 14 over the item's product information. The name of the product and the words "no serving size" are shown on display 18. If the user ants to indicate a serving size, the value can be adjusted using the set switches 32. When the correct serving size value is displayed, validation switch 26 is depressed.

The user is now prompted to set the time of consumption. The "hour" portion of the clock is blinking. The set switches 32 are pushed to change the numerical value of the blinking portion. When the correct number has been chosen, validation switch 26 is depressed and the next value, "minutes", is displayed. Minutes are set as described for hours. The validation switch 26 is depressed again.

Then, the message "repeat every 00:00 hours" is displayed on screen. This option can be used to repeat a schedule with a selected time interval. The first two digit field consists in units of the duration type displayed (in this case "hour(s)"). The two next digits are used to set unit fractions. The last field is the duration type that can be set to "hour(s)", "day(s)", " week(s)", and "month(s)". To set the time interval, set switches 32 are pushed to change the numerical value of the unit field, after the validation switch 26 is depressed. The fraction unit field will be blinking. The set switches 32 are pushed to change the numerical. The validation switch 26 is actuated again. The duration type is now blinking. The set switches 32 are actuated to choose the appropriate elapse type. Upon depressing the validation switch 26, the schedule will be recorded in the memory 16.

Mode V: Personal data update: To update the medical profile stored in the removable memory module 36, the 6-way switch 30 should be set on "personal data". Personal data defining the user medical profile such as size, age, weight, incompatibility or allergy to some food or to some medications can be updated. It should be noted that the memory module 36 could also be updated by retrieved data from a patient medical record maintained by an authorized health practitioner, or from hospital records. These data stored can thus include any information pertinent to items of interest to the user, and to the location for GPS-compatible systems.

Mode VI: Data Transfer: A serial or parallel port connection or infrared transmitter is provided for interchange of data between the device and an external device. To use the interface mode, the 6-way switch 30 is set to "interface". This mode can be used to send and receive data between the device and an external computer, as contemplated by FIG. 1b. Data such as the user-defined settings (such as the described items consumption schedule) and item product records can be downloaded from the device to the computer in order to be printed or for further analysis. Data can also be sent from the computer to the device, providing an alternate way to update the item database information. This latter technique is especially useful when updating the medical profile database as to medicines.

FIG. 4 is a summary figure having columns respectively showing three summary rows (a), (b) and (c) for three different typical applications of the invention as discussed above. The columns respectively represent: (I) the data scanned as described above for food (row a), medicine (row b), and food again (row c); and (II) the data in the medical profile database, as input either manually as in row (a) or either manually or by loading a prior items database (rows (b) and (c)). The last column III indicates the output analysis for the apparatus according to the methods of the invention for each of the combinations shown in row (a), columns I and II; row (b) columns I and II; and row (c) columns I and II.

Thus, for the example shown in row (a), the output provides a warning or equivalent notice to use as a function of the type, quantity, and input profile, for example, where the input profile is manually provided to the medical profile database. For row (b), the output analysis in column III shows or warns against medicine interaction based primarily on barcode readings of medicine as used or purchased. The Medical profile for this database depends on either a manual input or by a prior item database from prior scans. Finally, row (c) shows an output for a food/medicine interface based on product scans.

In summary, the medical user profile database should preferably include information related to allergies v. food, nutrients, chemical compounds found in the food or drugs, drug metabolism, and information about health v. food. The product data should preferably include nutrients, food/drug interference, drug/drug interferences, food/food interferences, and nutrient/chemical intolerances for the individual.

The foregoing description of the preferred embodiments of the method and apparatus of this invention are presented for illustration of the invention and for compliance with the requirements for a written description of the invention. The scope of the invention is thus measured by the appended claims and reasonable equivalents thereof.

What is claimed is:

1. A method of providing product information to a user, said product information pertaining to a product, said product being internally consumable by said user, said method comprising:

storing said product information within an items database, said items database being disposed within a remote computer;

storing user data within a profile database, said user data being information about said user, said profile database being located within said remote computer;

storing profile data within said profile database, said profile data being information about interactions between foods and medicines;

acquiring product data from a package for entry into an input device, said input device being separate and distinct from said remote computer, said input device being portable, said product data being additional information pertaining to said product;

searching said items database for said product information, said input device using said product data to search said items database for said product information;

consuming said product at a location;

recording said location; and providing said location to said remote computer.

2. The method as set forth in claim 1, wherein said product information includes barcode numbers, product name, product, produce suggested serving size, nutrients contained within the product, chemicals contained within the product, and processing techniques.

3. The method as set forth in claim 1, further comprising:

displaying said product information on a display, said display being located on said input device.

4. The method as set forth in claim 1, further comprising:

retrieving said product information from said items database, said input device retrieving said product information from said items database and comparing said received product information with said profile data.

5. The method as set forth in claim 4, further comprising:

warning said user of possible allergy or incompatibility to said product, said warning being based upon a result of said step of comparing.

6. The method as set forth in claim 1, wherein said input device includes an optical scanner.

7. The method as set forth in claim 6, wherein said package includes indicia for describing said product, said indicia being a barcode, said optical scanner entering said product data into said input device by scanning said barcode.

8. The method as set forth in claim 6, wherein said package includes indicia for describing said product, said indicia being text, said optical scanner entering said product data into said input device by scanning said text.

9. The method as set forth in claim 6, wherein said package includes indicia for describing said product, said indicia being handwriting, said optical scanner entering said product data into said input device by scanning said handwriting.

10. The method as set forth in claim 1, wherein said location is provided to said remote computer using a global positioning system.

11. The method as set forth in claim 1, wherein said items database is a removable storage medium.

12. The method as set forth in claim 11, wherein said removable storage medium is disposed on said input device.

13. The method as set forth in claim 11, wherein said removable storage medium is disposed on said central computer.

14. The method as set forth in claim 1, wherein said profile database is a removable storage medium.

15. The method as set forth in claim 14, wherein said removable storage medium is disposed on said input device.

16. The method as set forth in claim 14, wherein said removable storage medium is disposed on said central computer.

17. A method of providing product information to a user, said product information pertaining to a product, said product being internally consumable by said user, said method comprising:

storing said product information within an items database, said items database being disposed within a remote computer;

storing user data within a profile database, said user data being information about said user, said profile database being located within said remote computer;

storing profile data within said profile database, said profile data being information about interactions between foods and medicines;

acquiring product data from a package for entry into an input device, said input device being separate and distinct from said remote computer, said input device being portable, said product data being additional information pertaining to said product;

searching said items database for said product information, said input device using said product data to search said items database for said product information;

consuming said product on a consumption date and at a consumption time;

recording said consumption date and said consumption time; and providing said consumption date and said consumption time to said remote computer.

18. A device comprising:

an input device, said input device being separate and distinct from a remote computer, said input device being portable, product data being acquired product data from a package for entry into said input device, said product data being information pertaining to a product, said product being internally consumable by a user, said input device using said product data to search an items database for product information, wherein:

said remote computer contains said items database and a profile database, said product information is stored within said items database, said product information being additional information pertaining to said product, user data and profile data are stored within said profile database, said user data being information about said user, said profile data being information about interactions between [said] foods and medicines;

consuming said product at a location;

recording said location; and providing said location to said remote computer.

19. The device as set forth in claim 18, wherein said product information includes barcode numbers, product name, product, produce suggested serving size, nutrients contained within the product, chemicals contained within the product, and processing techniques.

20. The device as set forth in claim 18, wherein said product information on a display, said display being located on said input device.

21. The device as set forth in claim 18, wherein said input device retrieves said product information from said items database and compares said received product information with said profile data to provide a comparison.

22. The device as set forth in claim 21, wherein said input device warns said user of possible allergy or incompatibility to said product, said warning being based upon said comparison.

23. The device as set forth in claim 18, wherein said input device includes an optical scanner.

24. The device as set forth in claim 23, wherein said package includes indicia for describing said product, said indicia being a barcode, said optical scanner entering said product data into said input device by scanning said barcode.

25. The device as set forth in claim 23, wherein said package includes indicia for describing said product, said indicia being text, said optical scanner entering said product data into said input device by scanning said text.

26. The device as set forth in claim 23, wherein said package includes indicia for describing said product, said indicia being handwriting, said optical scanner entering said product data into said input device by scanning said handwriting.

27. The device as set forth in claim 16, wherein said location is provided to said remote computer using a global positioning system.

28. The device as set forth in claim 18, wherein said items database is a removable storage medium.

29. The device as set forth in claim 28, wherein said removable storage medium is disposed on said input device.

30. The device as set forth in claim 28, wherein said removable storage medium is disposed on said central computer.

31. The device as set forth in claim 18, wherein said profile database is a removable storage medium.

32. The device as set forth in claim 31, wherein said removable storage medium is disposed on said input device.

33. The device as set forth in claim 31, wherein said removable storage medium is disposed on said central computer.

34. A device comprising:

an input device, said input device being separate and distinct from a remote computer, said input device being portable, product data being acquired product data from a package for entry into said input device, said product data being information pertaining to a product, said product being internally consumable by a user, said input device using said product data to search an items database for product information, wherein:

said remote computer contains said items database and a profile database, said product information is stored within said items database, said product information being additional information pertaining to said product, user data and profile data are stored within said profile database, said user data being information about said user, said profile data being information about interactions between foods and medicines;

consuming said product on a consumption date and at a consumption time;

recording said consumption date and said consumption time; and providing said consumption date and said consumption time to said remote computer.

* * * * *